United States Patent [19]

Edmunds et al.

[11] Patent Number: 4,929,560
[45] Date of Patent: May 29, 1990

[54] RECOVERY OF TISSUE PLASMINOGEN ACTIVATOR

[75] Inventors: Timothy Edmunds, Weymouth; Susan F. Foley, Brighton, both of Mass.

[73] Assignee: Damon Biotech, Inc., Needham Heights, Mass.

[21] Appl. No.: 151,707

[22] Filed: Feb. 3, 1988

[51] Int. Cl.$^5$ .................... C12N 9/64; C12N 9/48; C12N 9/50

[52] U.S. Cl. .................... 435/226; 435/212; 435/219; 435/815

[58] Field of Search .............. 435/226, 212, 219, 215, 435/815; 424/94.64

[56] References Cited

U.S. PATENT DOCUMENTS

| | | | |
|---|---|---|---|
| 3,904,480 | 9/1975 | Hull et al. | 195/66 |
| 4,314,994 | 2/1982 | d'Hinterla | 424/95 |
| 4,317,882 | 3/1982 | Horiguchi et al. | 435/212 |
| 4,328,314 | 5/1982 | Horiguchi et al. | 435/212 |
| 4,505,893 | 3/1985 | Mori et al. | 424/94 |
| 4,540,486 | 9/1985 | Ramsden | 210/198.2 |
| 4,606,825 | 8/1986 | Crane et al. | 210/635 |

FOREIGN PATENT DOCUMENTS

| | | |
|---|---|---|
| 0041766 | 3/1981 | European Pat. Off. |
| 0093619 | 11/1983 | European Pat. Off. |
| 0196920 | 10/1986 | European Pat. Off. |
| 0211592 | 2/1987 | European Pat. Off. |
| 8601831 | 3/1986 | PCT Int'l Appl. |
| 8605514 | 9/1986 | PCT Int'l Appl. |
| 8701389 | 3/1987 | PCT Int'l Appl. |

OTHER PUBLICATIONS

Nau (preprint) "Chromatographic Purification and Analysis of Antibodies" (Research Specialty Products Division, J. T. Baker Chemical Company).

Nau (1986) "The Universal Approach to Immunoglobulin Purification" pp. 1–11.

Nau (1986) "A Unique Chromatographic Matrix for Rapid Antibody Purification" (Research Specialty Products Division, J. T. Baker Chemical Co.) Bio-Chromatography, vol. 1, No. 2, pp. 82–94.

Primary Examiner—Elizabeth C. Weimar
Assistant Examiner—Charles L. Patterson Jr.
Attorney, Agent, or Firm—Lahive & Cockfield

[57] ABSTRACT

Disclosed is a method of recovering tissue plasminogen activator from media and cell extracts. The method comprises contacting the tPA-containing solution with a silicaceous matrix material comprising covalently bound polymer having plural anionic groups. Selective elution of the tPA can produce eluants of high specific activity. The method can succeed in recovering greater than 90% of the tPA activity from the crude solution.

13 Claims, 1 Drawing Sheet

1 2 3 4 5 6 7 8 9

1 2 3 4 5 6 7 8 9

RECOVERY OF TISSUE PLASMINOGEN ACTIVATOR

BACKGROUND OF THE INVENTION

The present invention relates to a method of recovering enzymatically active tissue plasminogen activator (tPA) from a solution such as a culture medium or cell extract, using a chromatography resin. The invention is based on the discovery that a type of resin developed originally to selectively bind immunoglobulins binds tPA with great affinity, and therefore is useful for the commercial, large scale purification of tPA from tPA-containing solutions.

TPA is an enzyme which has the capacity to bind fibrin, and to catalyze the conversion of inactive plasminogen into the fibrinolytic enzyme, plasmin. Plasmin, in turn, degrades fibrin, a major component of blood clots, or thromboses. Therefore, tPA is a useful fibrinolytic agent for instigating the cascade mechanism which disrupts potentially fatal thromboses.

Native tPA is a glycoprotein having a molecular weight of about 66,000 daltons. It can be isolated from human blood as a single chain polypeptide, or as a dipeptide, consisting of one heavy (or A) chain disulfide bonded to one light (or B) chain, the B chain having the proteolytically active site. The single chain species may be preferred in pharmaceutical preparations over the two chain species. Further, the single chain form is believed to be the circulating species in vivo which is converted to the two chain form upon cleavage at the site of the fibrin clot, to which it binds.

Because of its extremely low concentration in the blood and tissue extracts, it is not economically feasible to purify tPA from these biological fluids for commercial use. In addition, circulating tPA has short-lived fibrinolytic activity, as it is rapidly cleared from the blood by the liver, and is readily inactivated by circulating serum proteases.

In an attempt to obtain clinically valuable amounts of tPA, cells which normally produce tPA, such as embryonic and human placenta-derived cell lines (e.g., U.S. Pat. Nos. 4,505,893 and 3,904,480), kidney and lung cells (e.g., U.S. Pat. No. 4,317,882), and human melanoma (e.g., EPO No. 0041766) have been cultured. To enhance the level of tPA synthesis by these cells, various nutritive inducers such as fumaric acid, malic acid, succinic acid, and/or glycolic acid (U.S. Pat. No. 4,328,314) and antimitotic agents such as colchicine, or podophylotoxin (U.S. Pat. No. 3,904,480) have been added to the culture media.

Alternatively, with the advent of recombinant DNA technology, cell lines which have been genetically engineered to produce large amounts of tPA have been developed and cultured. For example, transformed prokaryotic cell lines such as E. coli are said to synthesize and intracellularly deposit unglycoslyated tPA (e.g., EPO No. 0093619, EPO No. 0041766 and EPO No. 0196920). However, tPA production by recombinant means has been most successful in eucaryotic hosts such as mammalian cell lines (e.g., WO No. 86/05514) which are capable of the extensive posttranslational modifications characteristic of enzymatically active tPA.

The expressed tPA must then be recovered in active form from the cell extract or liquid growth media into which it has been secreted. A number of procedures are known by which such a recovery can be achieved including affinity chromatography, selective extraction, electrophoresis, and immunological methods. Recovery from culture media is a significant undertaking in that such media typically contain many other unrelated proteins, some of which having proteolytic activities. For example, serum-supplemented media are known to contain plasmin and other serum proteases which readily degrade tPA. Known purification procedures do not necessarily protect tPA from proteolytic degradation, although attempts have been made to do so by the addition of a metal chelating agent (e.g., U.S. Pat. No. 4,317,882) or various protease inhibitors (e.g., PCT No. 8601831) which offer at best only partial protection. Accordingly, known recovery methods are most effective when used to isolate tPA from serum-free solutions. However, most of these known methods are inefficient, and some introduce potentially toxic elements. In addition, purification procedures employing immunoaffinity chromatography may be quite costly when scaled up to meet commercial needs.

Therefore, for commercial quantitites of single chain tPA to be produced in an undegraded, enzymatically active form, large scale purification procedures are required which effectively and efficiently separate it from media before much of it is cleaved.

Accordingly, it is an object of the invention to provide a rapid, simple, and commercially viable method of isolating tPA from a tPA-containing solution. Another object is to provide a method of purifying enzymatically active single chain tPA from culture media. Yet another object is to provide a method of recovering enzymatically active tPA substantially free of other nonrelated proteins from a tPA-containing solution. It is also an object of the invention to provide a method of separating tPA from other proteins present in serum-supplemented media. It is a further object to provide a method of recovering enzymatically active single chain tPA in amounts useful for the large scale commercial production of pharmaceutical formulations containing tPA.

SUMMARY OF THE INVENTION

It has now been discovered that a chromatography resin of the type used to purify immunoglobulins is useful in recovering tPA from tPA-containing solutions. More specifically, it has been discovered that silicaceous matricies containing covalently bound polymers with multiple anionic groups surprisingly bind tPA preferentially to many other proteinaceous components in a solution, and permit selective elution of fractions rich in tPA. The use of such matricies in simple batch or chromatographic procedures can expedite and enhance the recovery of tPA from tPA-containing solutions including serum-free and serum-supplemented liquid culture media, extracts of cells which synthesize and intracellularly deposit tPA, and other solutions containing albumin, proteases, immunoglobulins, and diverse other proteins.

In its broadest aspects, this invention provides a method of recovering enzymatically active tPA from a tPA-containing protein solution. This method includes contacting the tPA-containing solution with a particulate, silicaceous matrix under conditions conducive for the binding of tPA to the matrix, separating unbound protein from the matrix, and releasing the bound tPA therefrom. The matrix comprises a covalently bound polymer having multiple cationic and anionic groups.

In one aspect, the present invention provides a method of recovering tPA in active, single chain form from culture media, including those which are supplemented with serum. Serum contains immunoglobulins which are known to bind to matricies of the type used in this invention, and serum proteases, which have the ability to degrade tPA. However, the matrix material used in this invention enables facile separation of tPA from harmful proteases, albumin, and other proteins by selective binding and elution as disclosed below.

The method of the present invention may be practiced by passing a tPA-containing solution over the matrix using a chromatographic techique, i.e., disposing the matrix in a column which is loaded, washed, and subsequently harvested. Alternatively, the method can be conducted using a solid phase batch extraction technique wherein the matrix material and the tPA-containing solution are mixed together.

The polymer which is covalently bound to the solid phase of the matrix of the present invention comprises, e.g., a polyethylene backbone, containing pendant anionic groups such as carboxylate groups. In a preferred embodiment, the polymer comprises a carboxylated polyethyleniminoalkyl trialkoxy silane, most preferably carboxylated polyethyleniminopropyl trimethoxysilane. The silane group is reactive and bonds covalently with free hydroxyl groups on the silica matrix. In this embodiment, the matrix is the carboxylated reaction product of particulate pore glass or silica and polyethyleneiminopropyl trimethoxy silane polymer having a molecular weight ranging from about 400 to about 1800 daltons. The glass may have an average particle diameter ranging from about 35 to 180 microns and an average pore size ranging from about 40 to 1000 Angstroms. Alternatively, the silica may have an average particle diameter ranging from about 3 to 70 microns and an average pore size of about 50 to 1000 Angstroms.

In a preferred aspect of the invention the matrix material contains from about 0.3 to 1.2 milliequivalents carboxy per gram matrix material.

In one embodiment, the contacting step of the invention is conducted at a pH of from about 4.0 to 6.0, but preferably at about 5.6. Generally, the tPA-containing solution should have an ionic strength no greater than 100 mM. The releasing step may be carried out at a pH of greater than 6.5 and at an ionic strength of about 100 millimolar or above. The releasing step also may be conducted at a pH of less than about 3.5. Between about pH-5 and pH-6.5, the bound tPA may be released with high ionic strength solutions, e.g., 0.5M or preferably 1.0M. Both the contacting and releasing steps may be conducted in the presence of epsilon amino caproic acid (EACA) and a detergent in a preferred aspect of the invention.

By practicing the method of the present invention, 90% or more of the tPA in a tPA-containing solution which has contacted the matrix material often can be recovered.

The foregoing and other objects of this invention, the various features thereof, as well as the invention itself, may be more fully understood from the following description, when read together with the accompanying drawings.

DESCRIPTION OF THE INVENTION

An efficient method of recovering undegraded and enzymatically active tPA from tPA-containing solutions has been devised which is simple, effective, and inexpensive.

Figure 1:
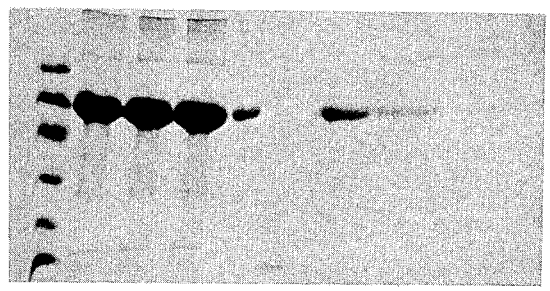
FIG. 1 is a representatiave COOMASSIE blue-stained SDS-polyacrylamide gel of the fractions obtained by the chromatography of conditioned, growth medium on an ABx column. Lane 1 contains low molecular weight standards, lane 2 contains the starting material loaded onto the gel; lanes 3 and 4 contain flow through; lanes 5 and 6 contain eluate obtained upon washing with Buffer A and B, respectively; lanes 7-9 contain eluate obtained upon development with Buffer C.
Figure 2:
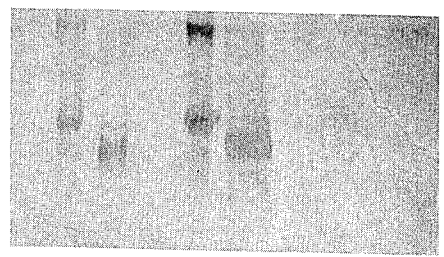
FIG. 2 is a representative silver stained (Gelcode) tPA purified from BSA-containing, conditioned (tPA-containing) medium, which had been fractionated according to the method of the present invention, and of the BSA-containing medium. Lanes 1 and 4 contain different amounts of BSA-containing medium; lanes 2 and 5 contain different amounts of ABx-Purified tPA; lane 7 contains a BSA standard; and lanes 3 and 6 are blank.

The method utilizes affinity chromatographic and extraction procedures which take advantage of the unexpected finding that known resins of the type previously used to purify and separate immunoglobulins (see U.S. Pat. No. 4,606,825) Preferentially bind tPA. In brief, the method comprises contacting a tPA-containing solution with the resin under conditions conducive to protein binding, separating unbound protein from the resin, and releasing bound tPA therefrom. The method can be used to recover tPA from any solution which contains tPA by itself or in a mixture with other proteins. Such solutions include, in particular, extracts of cells which express tPA, but which do not secrete it, and culture media which are serum-supplemented or serum-free. The SDS-polyacrylamide gel shown in FIG. 2 demonstrates the ability of the method to cleanly purify tPA from bovine serum albumin, a constituent of serum with a molecular weight similar to that of tPA, and a major protein component of many growth media.

The type of separation material suitable for use in the purification process comprises a particulate, silicaceous matrix such as one composed of silica gel or glass beads. These component particles may be of any size known to be useful in performing recovery procedures. However, silica particles having a diameter ranging from about 3 to about 70 microns, and glass beads having a diameter ranging from about 35 to about 180 microns are preferred. An average particle diameter of about 40 microns is the most useful for performing the method of the present invention. The particles also may be porous, the silica gel having a preferred pore diameter ranging from about 50 to 1000 Angstroms, and the glass beads having a preferred pore diameter ranging from about 40 to 1000 Angstroms.

Bound to the silicaceous particles are one or more polymers which have multiple anionic groups. The preferred polymers are polyethylene derivatized with carboxylate The polymer is preferably bound to the matrix through a silane group, and thus carboxylated polyethylenes having terminal reactive silane groups may be used to produce the separation matrix. The preferred polymer is a carboxylated polyethyleneiminoalkyl silane such as a polyethyleneiminopropyl trimethoxy silane. The molecular weight of the polymer generally may range from about 300 to about 2,000 daltons or higher. Although many different chemical side groups having a net negative or net positive charge may be useful, the most preferred anionic groups are carboxylate groups. A derivatized matrix material containing from about 0.3 to about 1.2 carboxy equivalents is the most desirable resin to effectively perform the method of the present invention.

The currently preferred matrix material useful in the present invention is sold by the J. T. Baker Chemical Co., Phillipsburg, N.J., under the trademark BAKERBOND ABx™. This material comprises a silica gel having an average particle diameter of 40 microns derivatized with a carboxylated polyethylenimine polymer. The method of manufacture of this preferred material and additional details about its structure are disclosed in U.S. Pat. No. 4,540,486, the disclosure of which is incorporated herein by reference.

The contacting step of the method of the present invention may be performed in any way which allows the charged groups of the derivatized matrix to come into contact with the solution. One preferred way of performing the contacting step employs an affinity chromatographic separation technique such as HPLC or traditional low pressure liquid chromatography wherein the tPA-containing solution is passed over and through the matrix. This can be accomplished by preloading the matrix into a chromatographic column preequilibrated with a buffer conducive to binding (equilibration buffer), and pouring the tPA-containing solution therethrough. The matrix material in the column may then be freed of any adventitiously-bound, extraneous material by washing with additional equilibration buffer.

An alternative contacting step uses a solid phase extraction procedure whereby the tPA-containing solution is mixed together with the matrix, forming a two phase mixture. The liquid and solid phases are then separated, and the matrix material is resuspended in additional equilibration buffer to remove extraneously-bound proteins therefrom.

In either case, the contacting step must be performed under conditions which enable the binding of tPA in the solution to the derivatized matrix. The lower the ionic strength, the better. Binding appears to be the result of the attraction and interaction of oppositely charged groups of the matrix and tPA. Therefore, conditions which maintain the charged nature of tPA and the matrix are important for success. Such conditions may be achieved by exposing the tPA and the matrix to solutions of suitable pH and ionic strength. For example, growth media used to culture tPA-producing cells and containing tPA (conditioned medium) may be adjusted such that the final concentrations of various components which affect the ionic strength and/or pH are compatible with tPA binding. In addition, the conditioned medium can be filtered to remove cell debris, and can be supplemented with a detergent, e.g., a commercially available, nonionic detergent such as a TWEEN detergent, e.g., Tween 80 (Sigma Chemical Co.), to discourage aggregation of protein. Preferred conditions for binding include the use of a solution or equilibration buffer having a pH between about 4.0 and about 6.0, with a pH of about 5.6 being the most preferable. Low ionic strength, e.g., less than 100 mM and preferably less than 25 mM, is also preferred.

The matrix containing bound protein is then washed, e.g., with equilibration buffer, to remove extraneous proteins and other contaminants.

The tPA releasing step must be carried out under specific conditions of ionic strength and pH to promote the most efficient removal of bound tPA from the matrix. This step may be conducted by exposing the tPA bound to the matrix to a solution (i.e. an elution buffer) which causes its release. For example, the solution may be poured through a column containing the bound tPA and matrix material or used to resuspend bulk matrix material. Preferred solutions are an elution buffer having a pH greater than about 6.5 and an ionic strength greater than about 100 millimolar, and a buffer having a pH above about 5, e.g., 5.6, and an ionic strength of about 1.0M. Alternatively, tPA may be eluted using a buffer having a pH of less than about 3.5. More than one elution buffer with increasing ionic strengths may also be used in sequence during the releasing step of the present invention.

Although other conditions which could enhance the success of the contacting and releasing steps may be substituted, the addition of epsilon amino caproic acid (EACA), which aids in tPA solubilization and acts as a protease inhibitor, and a detergent such as Tween-80 (Sigma Chemical Co.) to both the tPA-containing solution and the eluant is desirable.

The amount of tPA recovered from a solution by the method of the present invention may be determined by any number of known assay methods including, for example, immunoassay or activity assays. Generally, the method of the invention is able to recover in excess of 90% of the tPA activity in the crude extract, and results in solutions having very high enzymatic activity.

The following examples are presented to illustrate, but not to limit, the subject matter of the invention.

EXAMPLE 1

In this example, tPA is extracted from a typical serum-free growth medium supplemented with antibiotics.

A. Pretreatment:

Myeloma cells transformed to produce human tPA (see copending U.S. application Ser. No. 066,727 filed June 25, 1987) had been cultured in medium, referred to herein as "conditioned" (e.g., tPA-containing) medium. The conditioned medium is treated with EDTA to 5 mM and Tween 80 to 0.01%. The medium is then titrated to pH 5.6 with 6N HCL, and filtered through a 1.2 μm Sealkleen filter (Pall Biosupport) to remove cell debris.

B. Chromatography:

Four liters of the pretreated, conditioned medium are loaded at room temperature onto a Pharmacia K column (volume =3.17 ml) containing ABx (J. T. Baker Chemical Co., Phillipsburg, N.J.; 40 micron particle diameter), and run at 256 cm/hr. The column is washed with 20 column volumes of Equilibration Buffer A (10 mM morpholino ethane sulfonate (MES), 5 mM epsilon amino caproic acid (EACA), 5 mM EDTA, and 0.01% Tween 80, pH 5.6.). The protein on the column is then eluted with 10 column volumes each of four solutions containing different amounts of Elution Buffer B (500 mM NaOAc, 5 mM EACA, 5 mM EDTA, 0.01% Tween 80, pH 7.0): 20%, 40%, 60%, and 100% Buffer B: Buffer A. The column is then washed with 6 column volumes of Elution Buffer C (1M NaOAc, 5 mM EACA, 5 mM EDTA, 0.01% Tween 80, pH 7.0). The column eluate is monitored by UV absorption at 280 nm.

C. Electrophoresis:

The conditioned medium and column eluate are analyzed at different steps during the procedure by sodium dodecyl sulfate-polyacrylamide gel electrophoresis (SDS-PAGE gradient 7.5% to 20%) of trichloroacetic acid precipitated, or liquid samples, in accordance with the procedure of Laemmli, Nature (1970) 227:680–685. The gradient gel is stained with 0.25% Coomassie Blue, 50% methanol, 10% acetic acid, destained with 50% methanol, 10% acetic acid, and photographed.

Most of the tPA eluting from the column is found in the column fractions containing 60% and 80% Elution Buffer B. An SDS-PAGE comparison of the unconditioned growth medium and the pooled column fractions demonstrates that the proteinaceous material in these fractions is tPA cleanly purified from the BSA in the culture medium.

D. Activity Assay:

The medium and each of the column fractions analyzed by SDS-PAGE are analyzed for tPA activity by the Indirect tPA Assay. This assay is well known (see, e.g., "Current Status of Activity Assays for Tissue Plasminogen Activator", Enzyme Engineering, No. 7, Vol. 434). In the assay, the activity of the test sample is determined by measuring color development of the chromogenic substrate S-2251 as it is cleaved by plasmin. The plasmin is produced as plasminogen is cleaved by the tPA in the presence of fibrinogen. Activity is proportional to color intensity. The absorbance values of samples containing known concentrations of tPA were used to plot a standard curve (tPA concentration vs. $OD_{405}$). The concentration of tPA in each unknown sample were determined from this curve. The results are shown below in Table I.

TABLE I

| FRACTION | VOLUME | % OF TOTAL |
|---|---|---|
| orig pre-filter | 4 l | |
| orig material post filter | 4 l | 100% |
| Flow thru | 4 l | 25.0% |
| Wash | 65 ml | 0.8% |
| 20% B:A | 35 ml | 0 |
| 40% B:A | 40 ml | 1.2% |
| 60% B:A | 32.5 ml | 18.3% |
| 80% B:A | 30 ml | 50.2% |
| 100% B | 32.5 ml | 10.5% |
| 100% C | | <0.1% |

106% recovery of activity from the column

As can be appreciated from the foregoing, most of the enzymatic activity can be recovered from serum-free medium by following the method of the present invention.

EXAMPLE 2

A. Pretreatment:

Serum-free conditioned growth medium supplemented with antibiotics and EACA is pretreated and filtered as described in Example 1.

B. Chromatography:

92 liters of the pretreated, conditioned, serum-free medium are loaded at room temperature onto a Pharmacia K column (volume=750 ml) containing ABx (J. T. Baker Chemical Co.; 40 micron particle diameter), and the column is run at 191 cm/hr. After loading, the column is washed with 7 column volumes each of 100% Buffer A and 80% Buffer A/20% Buffer B (see EXAMPLE 1). The protein on the column is then eluted with 3 column volumes each of 100% Buffer B and 100% Buffer C (see EXAMPLE 1).

The column eluate is monitored by UV absorption as described in Example 1. Two peak fractions are obtained upon development with 100% Buffer B, and two additional peak fractions are obtained upon development with 100% Buffer C.

C. Electrophoresis:

The medium and column eluates are analyzed during the procedure by SDS-PAGE generally as described in EXAMPLE I. The majority of the tPA is eluted from the column with 100% Buffer C (peak 1).

D. Activity Assay:

The enzymatic activity of the tPA found in the medium and column eluate at each step during the procedure is analyzed by the Indirect tPA Assay. The results are shown below in Table II.

TABLE II

| FRACTION | VOLUME | % OF TOTAL |
|---|---|---|
| Orig pre-filter | 92 l | |
| Orig post filter | 92 l | 100% |
| Flow thru | 92 l | 0.8% |
| Wash | 5 l | <0.1% |
| 20% B:A | 5 l | <0.1% |
| Pre 100% B | 250 ml | <0.1% |
| 100% B (Peak 1) | 1 l | 0.5% |
| 100% B (Peak 2) | 1 l | 8.2% |
| 100% C (Peak 1) | 1 l | 80.0% |
| 100% C (Peak 2) | 1 l | 14.0% |

104% recovery of activity from the column

As can be appreciated from the foregoing, most if not all of the tPA-related enzymatic activity can be recovered in the serum-free medium by the method of the present invention.

EXAMPLE 3

In this example, tPA is extracted from a typical growth medium containing 1% donor calf serum (DCS) and 5 mM EACA.

A. Pretreatment:

The serum-containing conditioned growth medium is filtered and pretreated as described in EXAMPLE 1.

B. Chromatography:

50 liters of the pretreated and filtered conditioned medium are loaded onto a Pharmacia K column (volume=750 ml) at room temperature containing ABx (J. T. Baker Chemical Co., 40 micron Particle diameter), and the column is run at 229 cm/hr. After loading, the column is washed with 4 column volumes of 100% Buffer A and 5 column volumes of 80% Buffer A : 20% Buffer B. The protein on the column is then eluted with 3 column volumes of 100% Buffer B and 1 column volume of 100% Buffer C (see EXAMPLE 1).

The column eluate is monitored by UV absorption as described in EXAMPLE 1. Two UV-absorbing peak fractions are obtained upon development with 100% Buffer B.

C. Electrophoresis:

The medium and column eluate are analyzed during the procedure by SDS-PAGE as described in EXAMPLE 1. The majority of the tPA is eluted from the column with 100% Buffer B (peak 1).

D. Activity Assay:

The enzymatic activity of the tPA found in the medium and column eluate at each step during the procedure is analyzed by the Indirect tPA Assay as described above in EXAMPLE 1. The results are shown below in Table III.

TABLE III

| FRACTION | VOLUME | % OF TOTAL |
|---|---|---|
| Orig pre-filtration | 50 l | |
| Orig post-filtration | 50 l | 100% |
| Flow thru | 50 l | 1.2% |
| Wash | 3 l | <0.1% |
| 20% B:A | 4 l | <0.1% |
| 100% B | | |
| (Peak 1) | 2 l | 20.6% |
| (Peak 2) | 2 l | 70.9% |
| 100% C | 0.5 l | 1.6% |

94% recovery of activity from column.

As can be appreciated from the foregoing, the majority of the tPA-related enzymatic activity can be recovered from serum-containing media using the method of the present invention.

EXAMPLE 4

In this example, tPA is recovered from a typical growth medium supplemented with 2% DCS and 5 mM EACA.

A. Pretreatment:

Conditioned medium is filtered and pretreated as described above in EXAMPLE 1.

B. Chromatography:

34 liters of the filtered and pretreated conditioned medium are loaded at room temperature onto a Pharmacia K column (volume=750 ml) containing ABx (J. T. Baker Chemical Co.; 40 micron particle diameter), and the column is run at 250 cm/hr. After loading, the column is washed with 5 column volumes of 100% Buffer A and 3 column volumes of 80% Buffer A/20% Buffer B. The protein on the column is then eluted with 3 column volumes each of 100% Buffer B and a column volume of 100% Buffer C.

The column eluate is monitored by UV absorption as described in EXAMPLE 1. Two UV-absorbing peak fractions are obtained upon development with 100% Buffer B, and two peak fractions are obtained with 100% Buffer C.

C. Electrophoresis:

The medium and column eluate are analyzed during the procedure by SDS-PAGE as described in EXAMPLE 1. The majority of the tPA is eluted from the column with 100% Buffer B (peak 1).

D. Activity Assay:

The enzymatic activity of the tPA found in the medium and column eluate at each step during the procedure is analyzed by the Indirect tPA Assay as described in EXAMPLE 1. The results are shown below in Table IV.

TABLE IV

| FRACTION | VOLUME | % OF TOTAL |
|---|---|---|
| Orig pre-filter | 34 l | |
| Orig post-filter | 34 l | 100% |
| Flow thru | 32 l | <0.01% |
| Wash | 4 l | <0.01% |
| 20% B:A | 2 l | 0.26% |
| Pre-Peak | 0.4 l | 0.40% |
| 100% B | | |
| (Peak 1) | 1 l | 2.55% |
| (Peak 2) | 1 l | 22.38% |
| 100% C | | |
| (Peak 1) | 1 l | 76.09% |
| (Peak 2) | 1 l | 14.77% |

116% recovery from the column.

As can be appreciated from the foregoing, the majority of the tPA-related enzymatic activity can be recovered from serum-supplemented media by Practicing the method of the present invention.

EXAMPLE 5

In this example, tPA is recovered from a typical serum-free growth medium supplemented with a lipoprotein fraction without ethanolamine.

A. Pretreatment:

The conditioned medium is filtered and Pretreated as described above in EXAMPLE 1.

B. Chromatography:

97 liters of the filtered and pretreated conditioned medium are loaded at room temperature onto a Pharmacia K column (volume=500 ml) containing ABx (J. T. Baker Chemical Co.; 40 micron Particle diameter), and the column is run at 245 cm/hr. After loading, the column is washed with 12 column volumes of 100% Buffer A, followed by 6 column volumes of 100% "Buffer B" (10 mM NaOAc, 300 mM NaCl, 5 mM EDTA, 5 mM EACA, 0.01% Tween 80, PH 5.6 in this example). The protein on the column is then eluted with 100% Buffer C.

The column eluate is monitored by UV absorption as described in EXAMPLE 1. Three UV-absorbing peak fractions are obtained upon development with 100% Buffer C.

C. Electrophoresis:

The medium and column eluate are analyzed during the procedure by SDS-PAGE generally as described in EXAMPLE 1. The majority of the tPA eluted from the column with 100% Buffer C is found in Peak 1. A second gel (9%) was run and was stained with silver (Gelcode, Pierce Chemical Company,) instead of Coomassie blue. Two bands are visualized by this technique, the upper, higher molecular weight band being BSA, and the lower, lower molecular weight band being tPA. The majority of the tPA is eluted from the column with Buffer C, and is recovered in the peak 1 fractions.

D. Activity Assay:

The enzymatic activity of the tPA found in the medium and column eluate at each step during the procedure is analyzed by the Indirect tPA Assay as described in EXAMPLE 1. The results are shown below in Table V.

TABLE V

| FRACTION | VOLUME | % OF TOTAL |
|---|---|---|
| orig pre-filter | 98 L | — |
| orig post filter | 98 L | 100% |
| Flow thru 1 | 42 L | 0% |
| Flow thru 2 | 46 L | 0% |
| Wash 100% | 6 L | 0% |

TABLE V-continued

| FRACTION | VOLUME | % OF TOTAL |
|---|---|---|
| Buffer A Wash 100% Buffer B | 3 L | 0.06% |
| 100% C (Peak fraction 1) | 1 L | 67.4% |
| 100% C (Peak fraction 2) | 1 L | 14% |
| 100% C (Peak fraction 3) | 1 L | 8% |

89.4% recovery of activity from the column

The invention may be embodied in other specific forms without departing from the spirit and scope thereof. Accordingly, other embodiments are within the following claims.

What is claimed is:

1. A method for extracting tissue plasminogen activator (tPA) from a solution of tPA and other proteins, said method comprising the steps of:
   (a) containing a tPA-containing protein matrix under conditions in which tPA in solution with a particulate, silicaceous said solution binds to said matrix, said matrix comprising the covalently bound, carboxylated reaction product of said particulate, silicaceous matrix with polyethyleniminopropyl trimethoxy silane;
   (b) separating unbound protein from said matrix; and
   (c) releasing tPA from said matrix.

2. The method of claim 1 wherein said solution comprises a culture medium.

3. The method of claim 1 wherein said solution comprises a cell extract.

4. The method of claim 1 wherein said contacting step is conducted by passing said tPA-containing solution over said matrix using a chromatographic separation technique.

5. The method of claim 1 wherein said contacting step is conducted by mixing together said matrix and said tPA-containing solution to form a two-phase mixture using a solid phase extraction technique.

6. The method of claim 1 wherein said silicaceous matrix comprises particles selected from the group consisting of silica gel and porous glass beads.

7. The method of claim 1 wherein said matrix material comprises from about 0.3 to about 1.2 carboxyl milliequivalents per gram of said matrix material.

8. The method of claim 1 wherein said contacting step is conducted at a PH between about 4.0 and about 6.0.

9. The method of claim 8 wherein said contacting step is conducted at a pH of about 5.6.

10. The method of claim 1 wherein said releasing step is conducted at a PH greater than about 5.0 and at a ionic strength greater than about 100 millimolar.

11. The method of claim 1 wherein said releasing step is conducted at a pH less than about 3.5.

12. The method of claim 1 wherein said contacting and releasing steps are conducted in the presence of epsilon amino caproic acid and a detergent.

13. The method of claim 1 wherein said releasing step produces a fraction wherein tPA therein constitutes at least 90% of the tPA in said tPA-containing solution which has contacted said matrix.

* * * * *